(12) United States Patent
Killian et al.

(10) Patent No.: US 7,333,858 B2
(45) Date of Patent: Feb. 19, 2008

(54) PULSE BURST ELECTRICAL STIMULATION OF NERVE OR TISSUE FIBERS

(75) Inventors: Matthijs Killian, Mechelen (BE); Ernst von Wallenberg, Muellheim (DE); Guido Smoorenburg, Soest (NL)

(73) Assignee: Cochlear Limited, Lane Cove (AU)

( * ) Notice: Subject to any disclaimer, the term of this patent is extended or adjusted under 35 U.S.C. 154(b) by 145 days.

(21) Appl. No.: 11/092,771

(22) Filed: Mar. 30, 2005

(65) Prior Publication Data

US 2005/0222644 A1 Oct. 6, 2005

Related U.S. Application Data

(60) Provisional application No. 60/647,803, filed on Jan. 31, 2005, provisional application No. 60/557,713, filed on Mar. 31, 2004.

(51) Int. Cl.
*A61N 1/18* (2006.01)
(52) U.S. Cl. .............. 607/56; 607/55; 607/57; 607/66; 607/68; 607/72
(58) Field of Classification Search .......... 607/55, 607/57, 60, 137, 66, 68, 70, 72; 600/379
See application file for complete search history.

(56) References Cited

U.S. PATENT DOCUMENTS

| | | | |
|---|---|---|---|
| 3,563,246 A * | 2/1971 | Puharich et al. | 607/55 |
| 4,532,930 A * | 8/1985 | Crosby et al. | 607/57 |
| 4,592,359 A * | 6/1986 | Galbraith | 607/57 |
| 4,640,286 A * | 2/1987 | Thomson | 607/70 |
| 4,735,204 A * | 4/1988 | Sussman et al. | 607/60 |
| 5,271,397 A * | 12/1993 | Seligman et al. | 607/137 |
| 5,735,887 A * | 4/1998 | Barreras et al. | 607/60 |
| 6,078,838 A | 6/2000 | Rubinstein | |
| 6,289,247 B1 * | 9/2001 | Faltys et al. | 607/57 |
| 6,295,472 B1 | 9/2001 | Rubinstein et al. | |
| 6,631,295 B2 | 10/2003 | Rubinstein | |
| 6,845,271 B2 * | 1/2005 | Fang et al. | 607/74 |

* cited by examiner

*Primary Examiner*—Carl Layno
*Assistant Examiner*—Natasha Patel
(74) *Attorney, Agent, or Firm*—Connolly Bove Lodge & Hutz, LLP

(57) ABSTRACT

A method for stimulating nerve or tissue fibers and a prosthetic hearing device implanting same. The method comprises: generating a stimulation signal comprising a plurality of pulse bursts each comprising a plurality of pulses; and distributing said plurality of pulse bursts across one or more electrodes each operatively coupled to nerve or tissue fibers such that each of said plurality of pulse bursts delivers a charge to said nerve or tissue fibers to cause dispersed firing in said nerve or tissue fibers.

39 Claims, 10 Drawing Sheets

PULSE BURST ELECTRICAL STIMULATION OF NERVE OR TISSUE FIBERS

CROSS-REFERENCE TO RELATED APPLICATIONS

This application claims the priority of now abandoned U.S. Provisional Patent Application No. 60/557,713, entitled "Ramping Pulse Train Stimulation," filed on Mar. 31, 2004, and U.S. Provisional Patent Application No. 60/647,803, entitled, "Pulse Burst Stimulation and Its Use in Coding Strategies for Hearing Implants," filed on Jan. 31, 2005. The entire disclosure and contents of the above applications are hereby incorporated by reference herein.

BACKGROUND

1. Field of the Invention

The present invention relates generally to electrical stimulation devices and, more particularly, to pulse burst electrical stimulation of nerve or tissue fibers.

2. Related Art

There are several types of electrical stimulation devices that use an electrical signal to activate nerve or tissue fibers in a patient to stimulate an activity or response. A prosthetic hearing device or implant is an example of such a device that aids implant recipients who have a hearing deficiency. Prosthetic hearing implants apply one or more stimulation signals to the cochlea or auditory brainstem nuclei of the recipient to stimulate hearing. More particularly, such devices include a microphone that receives ambient sounds and a signal processor implementing a speech strategy which converts selected ambient sounds into corresponding stimulation signals. The signal processor controls an implanted unit to transmit the stimulation signals along an electrode array implanted within the cochlea of the recipient.

It has been generally well accepted that conventional prosthetic hearing devices fail to provide the desired natural perception of hearing due to their inability to precisely mimic the physiological firing pattern, or stimulation, which occurs in a healthy hearing ear.

SUMMARY

In one aspect of the invention, there is provided a method for stimulating nerve or tissue fibers. The method comprises generating a stimulation signal comprising a plurality of pulse bursts each comprising a plurality of pulses; and distributing said plurality of pulse bursts across one or more electrodes each operatively coupled to nerve or tissue fibers such that each of said plurality of pulse bursts delivers a charge to said nerve or tissue fibers to cause dispersed firing in said nerve or tissue fibers.

In another aspect of the invention, a method of stimulating nerve fibers using electrodes operatively coupled to nerve fibers is disclosed. The method comprises: generating a stimulation signal comprising a first plurality of pulse bursts having a first duration and a second plurality of pulse bursts having a second duration that is less than said first duration; distributing said first plurality of pulse bursts across one or more electrodes operatively coupled to nerve fibers responsive to low frequency stimulation; and distributing said second plurality of pulse bursts across one or more electrodes operatively coupled to nerve fibers responsive to high frequency stimulation.

In another aspect of the invention, a prosthetic hearing device is disclosed. The device comprises: means for generating a stimulation signal from an ambient sound; means for defining one or more pulse bursts in said stimulation signal; and means for distributing said pulse bursts across one or more electrodes so as to cause dispersed firing of nerve fibers.

BRIEF DESCRIPTION OF THE DRAWINGS

FIG. 118A shows the fiber population areas of stimulating nerves in the spiral ganglion operatively coupled to multiple electrodes, in accordance with an embodiment of the present invention.

DETAILED DESCRIPTION

Figure 1:
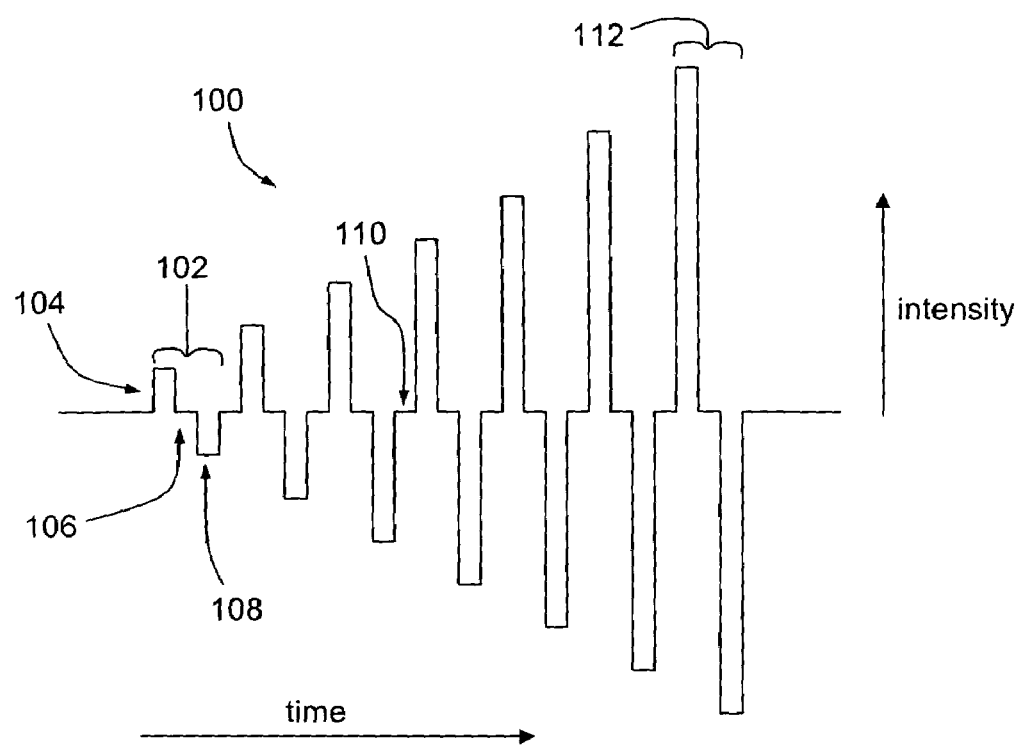
FIG. 1 shows a waveform of at least a portion of a stimulation signal comprising a pulse burst, in accordance with a embodiment of the present invention.

Aspects of the present invention are directed to an electrical stimulation device and method for stimulating nerve or tissue fibers. The stimulation signals each comprise a plurality of pulse bursts, with each pulse burst comprising a plurality of pulses. The pulse bursts deliver a charge to nerve or tissue fibers, typically via electrodes operatively coupled to the fibers, such that the charge delivered by the pulse bursts causes dispersed firing in the nerve or tissue fibers.

Embodiments of the present invention may be implemented in any medical device now or later developed. In one exemplary application disclosed herein, embodiments of the present invention are implemented in a prosthetic hearing device that generates stimulation signals in accordance with an implemented speech strategy to deliver a charge to auditory nerve fibers. It should be readily appreciated by those or ordinary skill in the art that the present invention may be implemented in other prosthetic hearing implants such as auditory brainstem implants (ABIs), as well as other implantable or non-implantable stimulating devices.

Embodiments of the present invention which are suitable for use in a prosthetic hearing device distribute the above-noted pulse bursts across one or more electrodes (also referred to as channels herein) to deliver a charge to a plurality of nerve fibers operatively coupled to the electrodes of an electrode array implanted in a recipient's cochlea. The charge delivered in accordance with the teachings of the present invention cause a response in the nerve fibers that more precisely mimics the natural dispersion and stochasticity of firing patterns of the natural ear.

The term "pulse burst" as used herein, refers to a series of successive stimulation pulses. A pulse burst generated in accordance with the teachings of the present invention has a discretely defined period such that the time duration between two successive pulses, referred to herein as intra-pulse gaps, is different from the time duration between pulse bursts, referred to herein as inter-pulse burst gap. An intra-pulse gap is the duration of substantial non-stimulating activity, i.e. when minimal or no charge is being delivered, between pulses within a pulse burst, and may also refer to the duration of substantial non-stimulating activity between the phases of a biphasic pulse. An inter-pulse burst gap is the duration of substantial non-stimulating activity between pulse bursts on the same channel.

As noted, embodiments of the present invention are described herein in the context of a prosthetic hearing device. There are a variety of prosthetic hearing devices in which the present invention may be used. Exemplary prosthetic hearing devices include, but are not limited to, those described in U.S. Pat. Nos. 4,532,930, 6,537,200, 6,565,503, 6,575,894 and 6,697,674, which are hereby incorporated by reference herein in their entirety.

One such exemplary device comprises an external component and an implanted component, such as Nucleus™ commercially available from Cochlear Limited, Australia. The external unit, when present, may be worn on the belt, clothing or behind the ear of the recipient. The external and internal units may communicate with each other by conventional telemetry techniques, such as an RF link. Depending on the desired function, such a prosthetic hearing implant may have a sensor (microphone) in the external unit which receives the sound and a signal/speech processor that converts the incident airborne sound into electrical stimulation signals.

The signal processor may have a variety of circuitry for implementing the speech strategy, which may include, among others, using filters using a Fast Fourier Transformation (FFT) to produce the stimulation signal. The electrodes may be arranged to be operatively coupled with the tonotopically-mapped cochlea in the inner ear. Conventional circuitry may be used to generate pulse bursts as described herein, and may be integrated into the implanted component of the prosthetic hearing implant, or may be a part of the external unit and transmitted to the implanted component. An example of an electrode used in a prosthetic hearing device is shown in U.S. Pat. No. 6,421,569, which is hereby incorporated by reference herein in its entirety.

There are several speech coding strategies that may be used when converting sound into an electrical stimulation signal. Embodiments of the present invention may be used in combination with a variety of speech strategies including but not limited to Continuous Interleaved Sampling (CIS), Spectral PEAK Extraction (SPEAK), Advanced Combination Encoders (ACE), Simultaneous Analog Stimulation (SAS), MPS, Paired Pulsatile Sampler (PPS), Quadruple Pulsatile Sampler (QPS), Hybrid Analog Pulsatile (HAPs), n-of-m and HiReS™, developed by Advanced Bionics. SPEAK is a low rate strategy that may operate within the 250-500 Hz range. ACE is a combination of CIS and SPEAK. Examples of such speech strategies are described in U.S. Pat. No. 5,271,397, the entire contents and disclosures of which is hereby incorporated by reference. The present invention may also be used with other speech coding strategies, such as a low rate strategy called Spread of Excitation which is described in U.S. Provisional No. 60/557,675 entitled, "Spread Excitation and MP3 coding Number from Compass UE" filed on Mar. 31, 2004, U.S. Provisional No. 60/616,216 entitled, "Spread of Excitation And Compressed Audible Speech Coding" filed on Oct. 7, 2004, and PCT Application WO 02/17679A1, entitled "Power Efficient Electrical Stimulation," which are hereby incorporated by reference herein.

Prosthetic hearing devices may locally store several speech strategies, such as in the form of a software program or otherwise, any one of which may be selected depending, for example, on the aural environment. For example, a recipient may choose one strategy for a low noise environment, like a conversation in an enclosed room, and second strategy for a high noise environment, like on a public street. The programmed speech strategies may be different versions of the same speech strategy, each programmed with different parameters or settings. The present invention may be implemented or programmed to correspond to these different environments by using different parameters and intensities for the pulse bursts. Adaptation to the aural environment may also be accomplished by changing processing parameters or settings of the speech strategy.

Traditional prosthetic hearing devices use speech strategies that generate stimulation signals comprising a single pulse to stimulate the auditory nerve. With single pulses the activity in the auditory nerve is highly synchronized which is in contrast to the normal ear in which the auditory nerve fiber activity is more stochastic in time and dispersed in space. In such conventional prosthetic hearing devices generating single pulse stimulation signals, a single current source generates the same signal that may be repeated over several electrodes. The resulting effect on the ear is that a single pulse does not achieve the stochastic and dispersed firing of the independent nerve fibers that occurs naturally in healthy ears. In contrast, certain embodiments of the present invention are an improvement over a single pulse as they generate more dispersed and stochastic activity in nerves and/or tissue fibers. This is described in greater detail below.

Other conventional prosthetic hearing devices implement a speech strategy that uses high rate stimulation to achieve stochasticity. Examples of such a method are described in U.S. Pat. Nos. 6,078,838, 6,295,472 and 6,631,295. Certain recipients may prefer high rate stimulation above low rate stimulation. This might be related to stochastic firing introduced by rates exceeding the maximum physiologically-possible neural fiber rate. With high rate stimulation the nerve fibers are continuously put in a refractory state which introduces stochastic firing. The high stimulation rate may be achieved by using a stimulation signal having a high rate pulse burst. The disadvantage of high rate strategies is that nerve fibers do not have an opportunity to recover as they are constantly in a refractory state. In contrast, certain embodiments of the present invention may introduce dispersed and stochastic firing at more normal physiological rates and give the nerve fibers a normal rest period to recover from their activation. This too is described in greater detail below.

Embodiments of the present invention may make it possible to introduce more dispersed firing among nerve fibers with conventional speech coding strategies, e.g. SPEAK, CIS, ACE etc., thereby improving perception. One advantage of such embodiments of the present invention is that a new speech strategy need not be developed to implement ramped pulse bursts. Instead, pulse bursts of the present invention may be used in place of the single pulse generated by conventional hearing implants. As one of ordinary skill in the art would understand, the mechanisms for defining the pulse bursts are flexible and may be part of the speech processor software or circuitry in the external or implant unit, or the stimulation pulse generator in the implanted unit. It should also be appreciated that the above and other embodiments provide additional advantages. For example, certain embodiments provide an audiologist with the capability of measuring the threshold (T) and comfort (C) levels for individual recipients of a prosthetic hearing device.

Details of a variety of embodiments of the present invention are described next below with reference to the figures.

FIG. 1 shows an exemplary pulse burst 100 generated in accordance with the teachings of one embodiment of the present invention. Pulse burst 100 is comprised of a plurality of biphasic pulses 102 in this example. As one of ordinary skill in the art would appreciate, there are a myriad of pulse waveform parameters which may be used to define each pulse of a pulse burst, as well as the pulse burst itself. In addition to the above intra-pulse gap and inter-pulse burst gap, these include, but not limited to, an intensity function of the pulse burst, a pulse rate, an amplitude of the pulse, etc. These and other waveform parameters are described in detail herein below.

Referring to the example shown in FIG. 1, pulse waveform parameters can be used to define a pulse such as biphasic pulse 102. Each pulse has an initial phase ($PW_1$) 104, an intra-pulse gap (IPG) 106, and a reverse phase ($PW_2$) 108. There is also an intra-pulse gap 110 between successive pulses 102. This particular example of pulse burst 100 is shown to linearly increase in intensity so that the final pulse 112 has a larger amplitude than initial pulse 102. The parameters of pulses 102 may vary, as described in further detail below, depending, for example, on the perception responses of the recipient and/or the implemented speech strategy.

Although the exemplary the pulse burst in FIG. 1 is shown to increase in intensity, a pulse burst may also have a constant intensity, decreasing intensity, or varying intensity. A pulse burst with a constant intensity may have different phase widths for each pulse to increase the intensity of the pulses. A pulse burst with a decreasing intensity may have an initial pulse burst with a relatively larger amplitude than the remaining pulses in the pulse burst. A pulse burst with a varying intensity pulse may increase and decrease during the pulse burst period. Additional combinations pulse bursts having different intensities and durations may be used on multiple channels when delivering the stimulation signal as a plurality of pulse bursts.

Figure 15A:
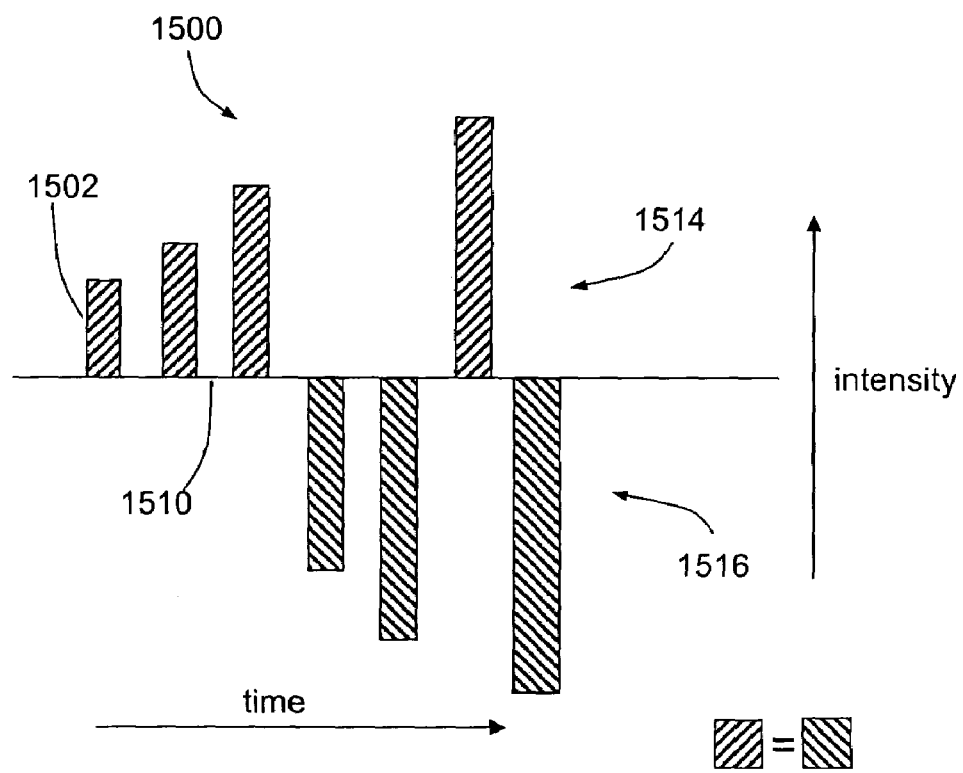
FIGS. 15A and 15B show a stimulation signal comprising a ramping pulse burst having monophasic pulses in accordance with an embodiment of the present invention.
Figure 15B:
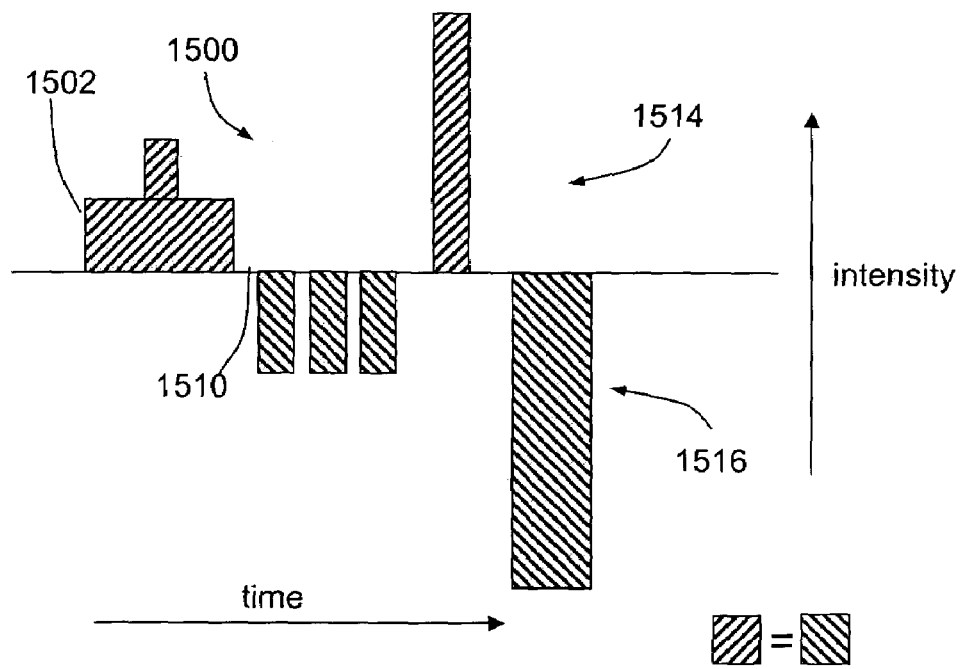

In some embodiments, each pulse burst is substantially balanced to prevent a charge from remaining in the nerve fiber. For example, in FIG. 1, pulse burst 100 comprises biphasic pulses each with substantially the same initial and reverse phase 104, 108. It should be appreciated, however, that monophasic stimuli that in total produce a balanced pulse burst may also be used. For example, as shown in FIGS. 15A and 15B, several monophasic pulses 1502 in a pulse burst 1500 are in balance such that the total charge of positive monophasic pulses 1514 equals the total charge of negative monophasic pulses 1516. Monophasic pulses 1502 may differ in amplitude, duration, waveform, and have different intra-pulse gaps 1510. One advantage of such embodiments is that the hearing implant may use lower current levels in generating the stimulation signals.

Figures 2A, 2B:
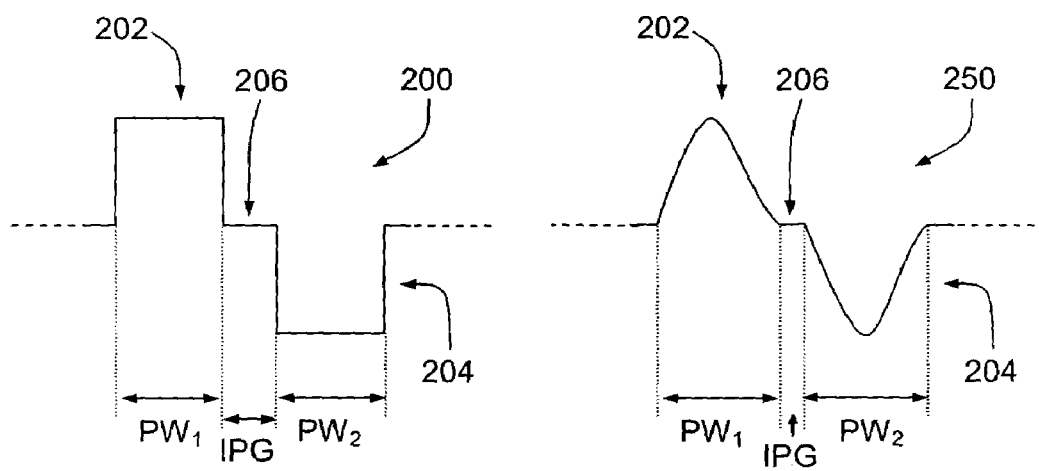
FIGS. 2A, 2B, 2C and 2D show waveforms of a single pulse that may be included in a stimulation signal containing one or more pulse bursts, in accordance with an embodiment of the present invention.
Figure 2C:
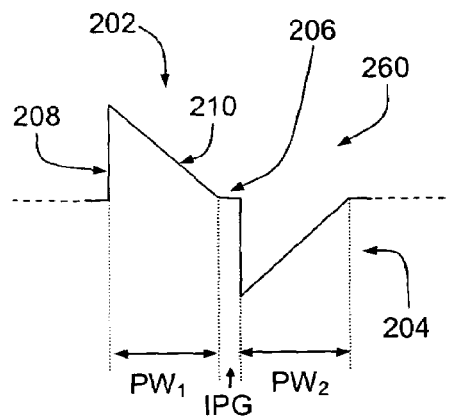
Figure 2D:
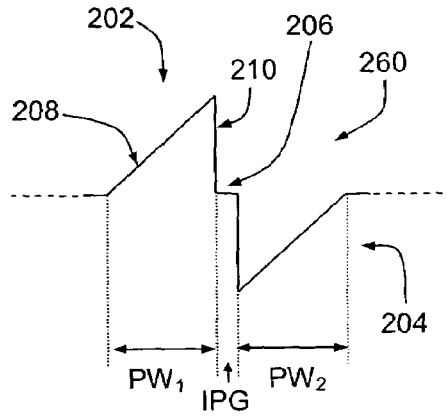

FIGS. 2A, 2B, 2C and 2D are illustrative waveforms of an individual biphasic pulse of a pulse burst generated in accordance with the teachings of the present invention. Each pulse 200 in the pulse burst has an initial phase pulse width ($PW_1$) 202, a reverse phase pulse width 204 ($PW_2$) and an intra-pulse gap (IPG) 206. The waveform of pulse 200 shown in FIG. 2A is a square or staircase waveform, while the waveform of the pulse 250 shown in FIG. 2B is a sinusoidal waveform. In FIGS. 2C and 2D, pulse 260 has a saw tooth waveform. In FIG. 2C, raising edge 208 has a larger slope than trailing edge 210 in FIG. 2C, while in FIG. 2D the slope of raising edge 208 is smaller than trailing edge 210. Each pulse of a pulse burst may have a different waveform, duration, rate, amplitude, etc, as described elsewhere in this application. It should be readily understood to those skilled in the art that the waveform pf pulses generated in accordance with the present invention may be other than that illustrated in FIGS. 2A-2D. It should also be appreciated that the pulses in a pulse burst may have a constant waveform throughout the entire pulse burst, or may have a variety of pulse waveforms.

Each pulse burst of a stimulation signal generated in accordance with the teachings of the present invention may replace a single pulse in a conventional prosthetic hearing implant and/or speech strategy. The number of pulses within a pulse burst that may be used in currently available coding strategies depends on the maximum stimulation frequency of the hearing device (14400 Hz for Nucleus™ Contour™ implant model number CI24R; 32 kHz for Nucleus™ Contour™ implant model number CI24RE) and the total stimulation rate of the implemented speech coding strategy. The number of pulses in a pulse burst also may be related to the implemented speech strategy. For example, when embodiments are implemented in a conventional low rate system, such as SPEAK, with a stimulation rate of 250 Hz and having 8 maxima, i.e. channels which are stimulated based on the strategy, the total stimulation rate is 2000 Hz (=8× 250). This implies that if a single pulse of a conventional system can be replaced with a ramping pulse burst of the present invention if the duration of each pulse burst is less than or equal to 500 µs. For example, a pulse having a $PW_1$ and $PW_2$ of approximately 25 µs and an IPG of 8 µs may provide a total stimulation rate of 14400 Hz. This may allow up to 7 pulses into the ramping pulse burst. As noted, the quantity of pulses in a pulse burst may vary depending on the parameters used and stimulation requirements to achieve the desired perception.

It should be understood to those skilled in the art that the phase width or duration for each biphasic pulse in the pulse burst may be different for the initial and reverse phase. For example, the combination of phase widths for both phases in a biphasic pulse may equal approximately 5 µs to 1000 µs. Preferably, the combined phase width may equal approximately 20 µs to 100 µs. When using a monophasic pulse, the single pulse may have a width from approximately 5 µs to 1000 µs. Preferably, the single pulse may have a width of approximately 20 µs to 100 µs. The duration or width for the IPG may vary from approximately 5 µs to 500 µs. Preferably, the IPG may equal approximately 6 µs to 50 µs. The phase widths and IPGs for the pulses may vary within a pulse burst or between pulse bursts in a stimulation signal and may be independent of each other, as shown in FIGS. 15A and 15B.

In one embodiment of the present invention, a pulse burst may be generated to stimulate different fiber populations in the nerve and/or tissue, thereby introducing "controlled" dispersion in the neural population. A preferred pulse burst, or set of stimuli, may have a set of pulses with successively increasing intensity and/or rate. At low intensity, the nearby nerve fibers may be activated and more distant fibers are recruited when the intensity is increasing during the ramping of the pulse burst. For example, the nerve fibers stimulated by a low intensity pulse within a pulse burst are more likely to be operatively coupled and in close physical proximity to the stimulating electrode. Nerve fibers that are operatively coupled and in not physically close to the electrode are more likely to not be stimulated by such a low intensity pulse. However, as successive pulses of the stimulating pulse burst increase in amplitude or intensity, nerve fibers operatively coupled and located away from the electrode may be recruited and activated. In other words, higher amplitude pulses in the pulse burst may stimulate those nerve fibers that were stimulated by the lower amplitude pulses, as well as those nerve fibers located away from the electrode.

In one embodiment, each pulse within a pulse burst has an amplitude that is greater than the amplitude of the immediate preceding pulse in the pulse burst, thereby providing a continually-increasing intensity over the pulse burst. Such a ramping pulse burst may constantly stimulate nerve and/or tissue fibers during the time the charge is delivered ("burst period" herein). Each successive pulse of a ramping pulse burst generated in accordance with the above and other embodiments may also recruit additional nerve fibers as compared to the prior pulse of the pulse burst. By recruiting nerve fibers using ramped pulse bursts, embodiments of the present invention may more precisely mimic natural dispersed and stochastic firing patterns to enhance sound perception of recipients. As used herein, "dispersed firing" refers the effect caused by an electrical stimulation signal that causes the nerve and/or tissue fibers to fire or react in a slowly recruiting and more scattered pattern. The effects of such a ramping pulse burst are illustrated in FIGS. 14A and 14B.

Figure 14A:
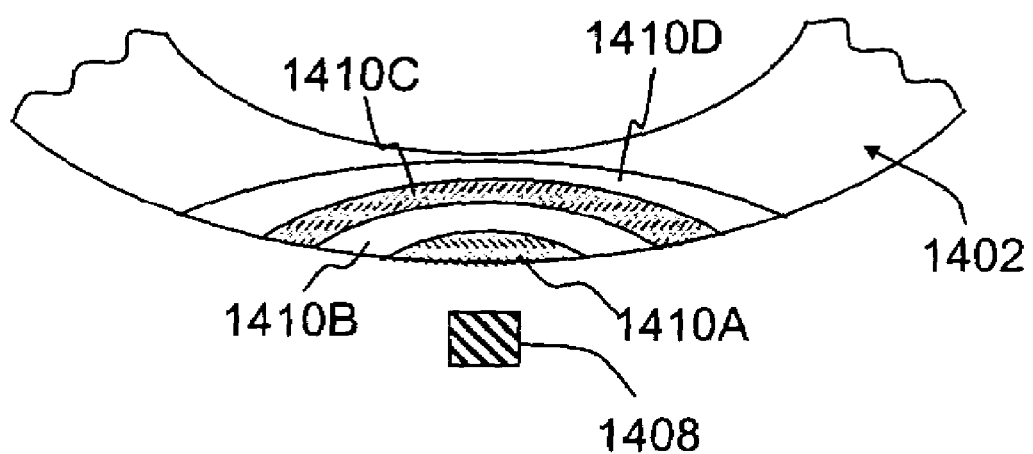
FIG. 14A shows the fiber population areas of stimulating nerves in the spiral ganglion that are operatively coupled to a single electrode, in accordance with an embodiment of the present invention.
Figure 14B:
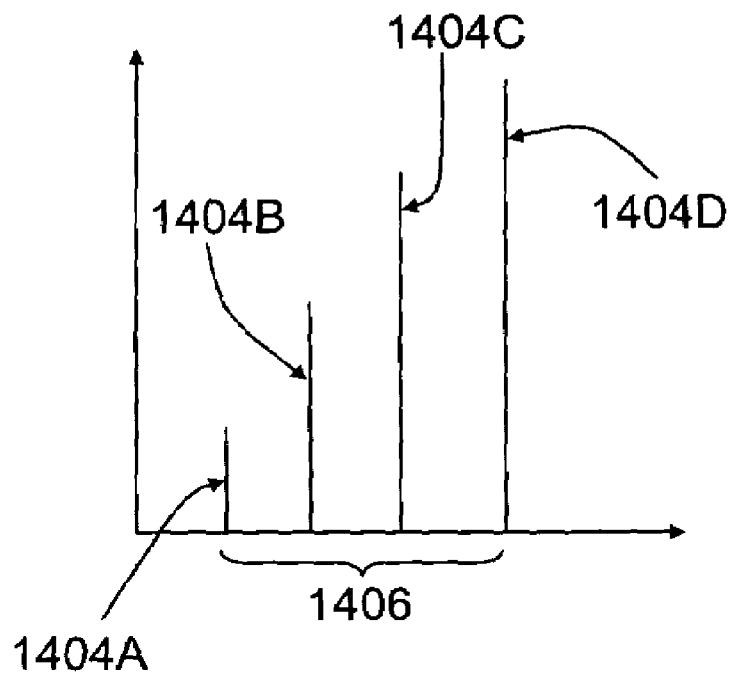
FIG. 14B shows a pulse burst used to generate the stimulation shown in FIG. 14A.

FIG. 14A is a schematic representation of a portion of a spiral ganglion nerve fiber showing the fiber population areas that are stimulated by an operatively coupled electrode. FIG. 14B shows one pulse burst of a stimulation signal which can be generated to deliver a charge which causes the dispersed firing activity shown in FIG. 14A. The nerves in spiral ganglion 1402 may be kept in a stimulated state because each pulse 1404 within a pulse burst 1406 is of a greater amplitude than its immediate preceding pulse 1404. An electrode 1408 is operatively coupled to spiral ganglion 1402 to deliver pulse burst 1406 to the region of spiral ganglion 1402 immediately adjacent to electrode 1408.

Electrode 1408 delivers a charge to fiber population area 1410A with pulse 1404A; delivers a greater charge to fiber population area 1410B with pulse 1404B; etc. The area of each fiber population area 1410 which receives the delivered charge increases with each successive pulse 1404 in pulse burst 1406 due to the greater charge delivered with each of the successive pulses.

It should be appreciated that the above change in amplitude may create a stochastic response in the activated nerve fibers. In addition, pulse 1404A may activate fiber population area 1410A multiple times, which may cause the neurons within that area to respond stochastically. Each pulse 1404 may be repeated multiple times further causing the neurons in each population area 1410 to stochastically respond to the delivered charge.

As will be described in greater detail below, the above effects may also be attained by altering the duration, rate or other parameters of the pulses in the pulse burst. As one of ordinary skill in the art would appreciate, loudness increases with pulse rate and, therefore, pulse rate may be used to code loudness. It should also be appreciated that dispersed firing might also help in prostheses that electrically stimulate muscles directly or indirectly through the nerves connected to the muscle.

It should be understood to those skilled in the art that the intensity function of the pulse burst may be represented by a variety of different functions. A few functions are shown in FIGS. 3A-3D for illustrative purposes where reference numeral 300 refers to the "loudness" or intensity of the first pulse burst and reference numeral 302 refers to a next successive pulse burst. The function of two addition pulse bursts are illustrated as well. In each of these examples, the four successive pulse bursts have a similar intensity function. The individual pulses of the pulse burst are not illustrated in FIGS. 3A-3D for clarity.

Figure 3A:
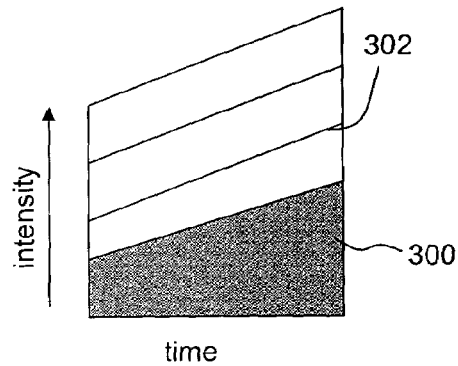
FIG. 3A is a graphic representation of the intensity levels of a series of pulses in successive pulse bursts burst, wherein the intensity of the pulse bursts can be represented by a similar linearly increasing intensity function, in accordance with an embodiment of the present invention.
Figure 3B:
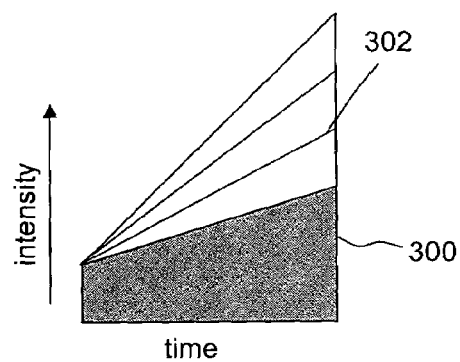
FIG. 3B is a graphic representation of the intensity levels of a series of pulses in successive pulse bursts, wherein the intensity of the pulse bursts can be represented by a progressively increasing linear intensity function, in accordance with an embodiment of the present invention.
Figure 3C:
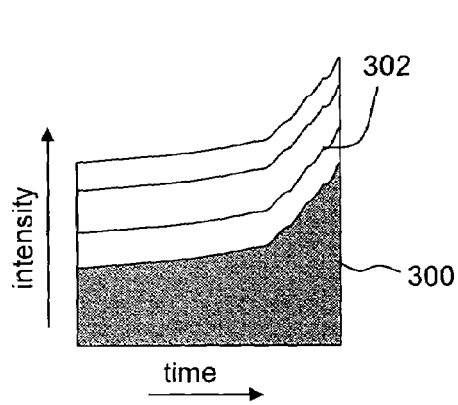
FIG. 3C is a graphic representation of the intensity levels of a series of pulses in successive pulse bursts, wherein the intensity of the pulse bursts can be represented by a substantially similar exponential intensity function, in accordance with an embodiment of the present invention.
Figure 3D:
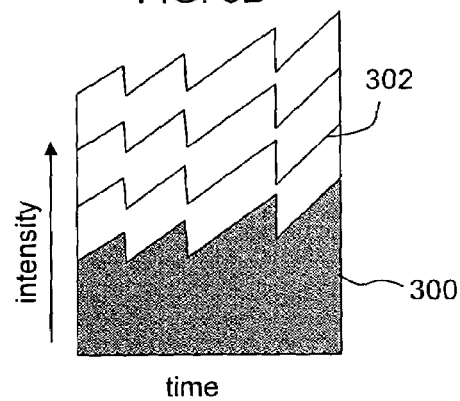
FIG. 3D is a graphic representation of the intensity levels of a series of pulses in successive pulse bursts, wherein the intensity of the pulse bursts can be represented by a substantially similar staggered intensity function in accordance with an embodiment of the present invention.

As shown in FIG. 3A, there is a substantially similar linearly increase in the intensity function the illustrated pulse bursts with each successive pulse burst having a greater intensity that the previous pulse burst. FIG. 3B shows an intensity function for progressively increasing linear pulse bursts with each successive pulse burst having a same starting value and an ending intensity value that is greater than the previous pulse burst. FIG. 3C shows pulse bursts with substantially similar exponential intensity function with each successive pulse burst having a greater intensity that the previous pulse burst. FIG. 3D shows pulse bursts having a substantially similar staggered intensity function with each successive pulse burst having a greater intensity that the previous pulse burst.

Figure 4:
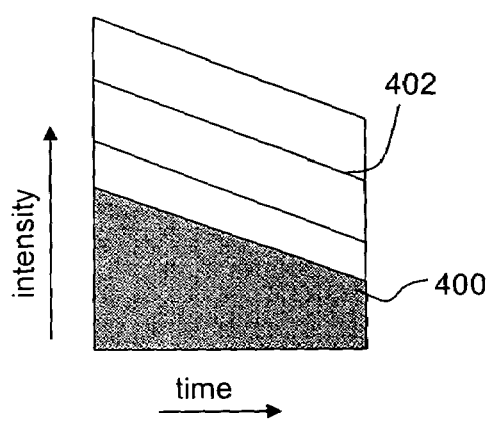
FIG. 4 shows a plurality of overlaid waveforms showing a series of pulse bursts having similar intensity functions which decrease over time in accordance with an embodiment of the present invention.
Figure 5:
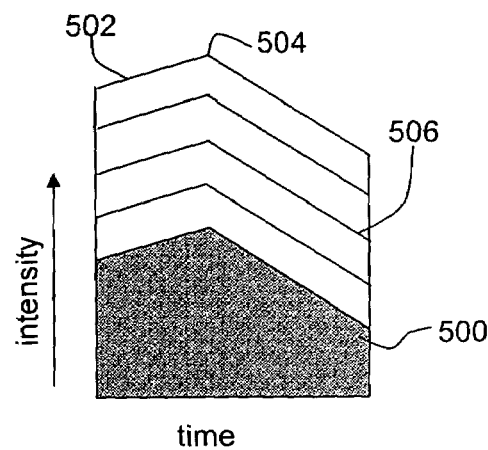
FIG. 5 shows a plurality of overlaid waveforms showing a series of pulse bursts having similar intensity functions which varies over time in accordance with an embodiment of the present invention.
Figure 16:
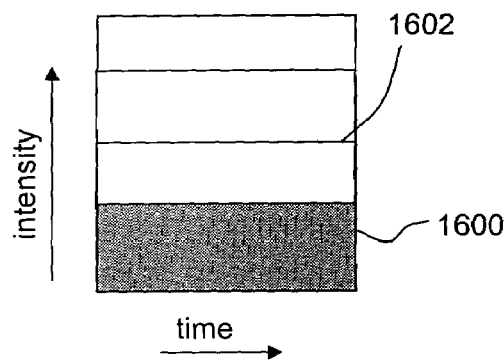
FIG. 16 shows a plurality of overlaid waveforms showing a series of pulse bursts having similar intensity functions which remain constant in intensity over time in accordance with an embodiment of the present invention.

It should be appreciated that embodiments of the present invention can generate stimulation signals comprising pulse bursts having intensity functions other than those shown in FIGS. 3A-3D including but not limited to triangular, staggered, staircase, saw tooth, or sinusoidal. It should be understood to those skilled in the art that the intensity of a pulse burst may decrease or vary over time using a number of different functions, including linear, linearly increasing/decreasing slope, exponential, staggered, among others. For example, in addition to the exemplary pulse bursts described above with reference to FIGS. 3A-3D, the intensity of a pulse bursts may decrease 402, as illustrated in FIG. 4, or a pulse bursts may vary over time, as illustrated in FIG. 5. In FIG. 5, the intensity 500 of the pulse bursts increases 502 to an apex 504 and then decreasing 506. In FIG. 16, the intensity of each pulse remains constant 1602, while each successive pulse burst in the stimulated signal increases.

Figure 17A:
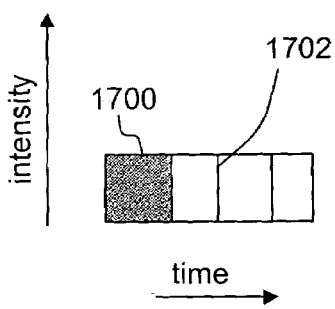
FIG. 17A shows a plurality of overlaid waveforms showing a series of pulse bursts having similar intensity which increase in duration over time in accordance with an embodiment of the present invention.
Figure 17B:
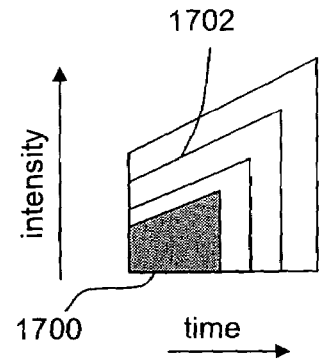
FIG. 17B shows a plurality of overlaid waveforms showing a series of pulse bursts having similar intensity functions and which increase in duration over time in accordance with an embodiment of the present invention.

It should be understood that the intensity (loudness) may also be delivered a charge by increasing the duration of pulses in a pulse burst as shown in FIGS. 17A and 17B. In FIG. 17A, the loudness 1700 may be increase in duration 1702 with each successive pulse. In FIG. 17B, each successive pulse may increase 1702 in intensity and duration.

The intensity functions shown in FIGS. 3, 4, 5, 16 and 17 may also be used to measure behavioral thresholds and comfort levels (T and C levels) pulse burst repetitions the each of the intensity functions. Threshold level (T Level) is the minimum level of electrical stimulation required at each electrode for the recipient to first hear a sound using a hearing implant. Each recipient may respond to electrical stimulation at different levels. Maximum Comfort Level (C Level) refers to the highest electrical stimulation level that does not produce an uncomfortable loudness sensation for the recipient. The T and C levels may be adjusted, for example, while the implant is being used.

Figure 6:
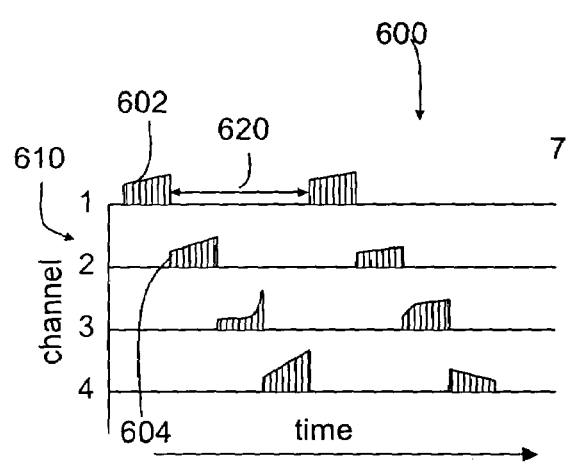
FIG. 6 shows a stimulation signal containing several pulse bursts produced by a single current source and distributed across four channels of a prosthetic hearing implant, in accordance with an embodiment of the present invention.

In the embodiment shown in FIG. 6, there are four channels that correspond to four electrodes that are operatively coupled to four groups of nerve fibers in the cochlea. It should be understood that more channels may be used depending on the capabilities of the prosthetic hearing implant. In addition, a selected number of channels may be used depending on the strategy used (e.g. ACE is a roving strategy in which n of m electrodes are activated during every cycle). In typical prosthetic hearing implant devices, there may be as many as 22-24 electrodes. Depending on the strategy used, a portion of the 22-24 electrodes of such a device may be activated to transmit each stimulation signal.

FIG. 6 shows a CIS strategy on 4 channels in where each pulse of the conventional stimulation signal may be converted into or defined as a pulse burst. The individual pulses in each pulse burst may be monophasic or biphasic and may have a variety of waveforms, amplitudes, durations, intra-pulse gaps, widths, etc., as described above. The stimulation signal 600 may start with pulse burst 602 on channel 1 of an electrode array 610. Once one pulse burst 602 ceases, a second pulse burst 604 is distributed on channel 2. This process may be repeated on the remaining channels and repeated on the same channel when stimulating the nerve fibers with the stimulation signal. Since one current source is used, only one pulse burst may be activated on one corresponding electrode within array 610 at any given time. Each pulse burst over a period of time may have a different intensity corresponding to the sound signal inputted into the prosthetic hearing device. Also, the inter-pulse burst gap 620 is larger than the intra-pulse gaps (not shown). In addition, while the channels 1 and 2 are shown in sequence, it should be understood that any sequence of pulse bursts 602 and 604 on any number of channels may be used to stimulate the sound signals inputted into the prosthetic hearing implant (not shown).

Figure 7:
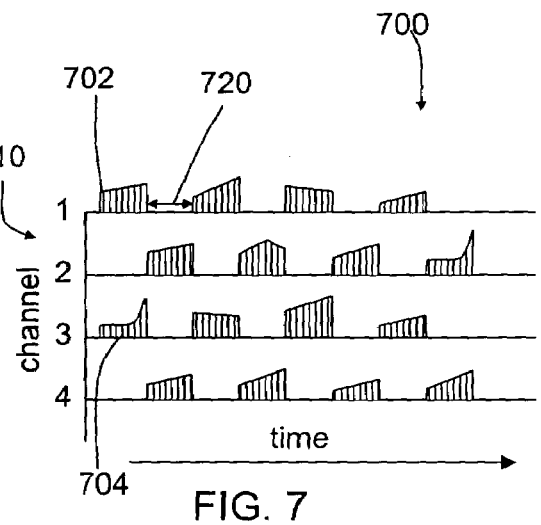
FIG. 7 shows a plurality of pulse bursts produced by two current sources on four channels, in accordance with an embodiment of the present invention.

FIG. 7 shows a CIS strategy that uses two current sources (not shown) so that two pulse bursts of a stimulation signal 700 may be sent on two channels at substantially the same time. At substantially the same time that pulse burst 702 is distributed on channel 1, pulse burst 704 is also distributed on channel 3. N pulse bursts may be sent on M channels, including successively using the same channel if necessary to stimulate the nerve fibers with stimulation signal 700. Also, the inter-pulse burst gap 720 is larger than the intra-pulse gaps (not shown). The pulses of each pulse burst may be generated from two separate sources and may have any of the parameters, as discussed above.

Figure 8:
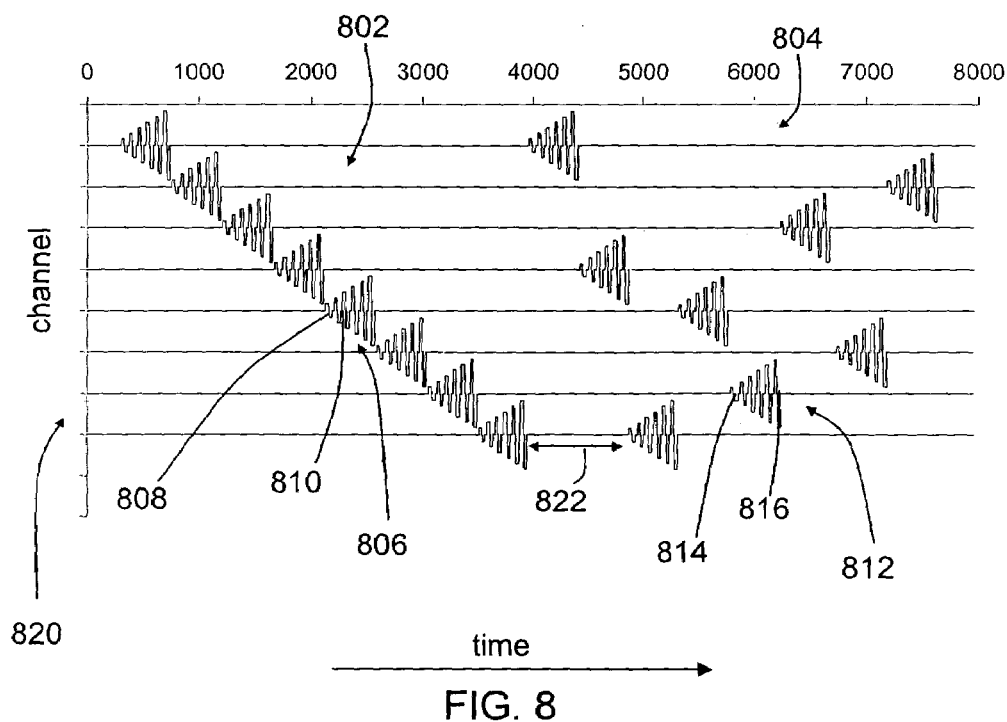
FIG. 8 shows ramping pulse bursts that are repeated on channels, in accordance with an embodiment of the present invention.

FIG. 8 shows a stimulation signal 802 having a plurality of pulse bursts repeated on adjacent channels (representing CIS) and a stimulation signal 804 having a plurality of pulse bursts repeated on non-adjacent channels (representing ACE). Pulse bursts 806 of stimulation signal 802 have pulses 808. Each pulse 808 is separated by an intra-pulse gap (IPG) 810. Pulse bursts 806 may be repeated successively on each channel. In addition, pulse burst 806 may vary, using the parameters described throughout this application, to stimulate the incoming sound to the nerve fiber. Pulse bursts 812 of stimulation signal 804 have pulses 814. Each pulse 814 is separated by an intra-pulse gap (IPG) 816. Pulse bursts 812 may be repeated non-successively on each channel. In addition, pulse burst 812 may vary, using the parameters described throughout this application, to stimulate the incoming sound to the nerve fiber. Each channel of the array 820 represents a different frequency band analyzed with a filter or Fast Fourier Transform Analysis. Pulse burst 806 and pulse burst 812 are separated by an interval or inter-pulse burst gap 822, which is larger than the IPGs 810 and 816. Pulse bursts 806 and 812 may create dispersion in the nerve fiber population (not shown) by using a ramping intensity. Other combinations of applying stimulation signals 802 and 804 may use pulse bursts that are different on each channel and/or applied to non-adjacent channels are envisaged by embodiments of the present invention. Pulse bursts 806 and 812 shown in FIG. 8 may be used in combination with SPEAK, ACE, CIS and other speech strategies.

Figure 9:
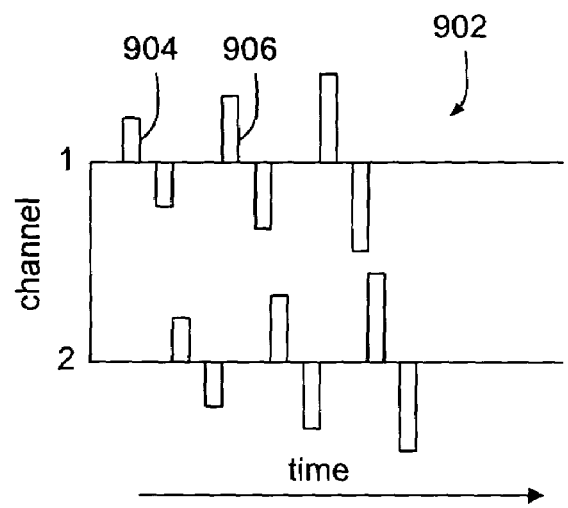
FIG. 9 shows repeating pulses of a pulse burst interleaved on two channels, in accordance with an embodiment of the present invention.
Figure 10:
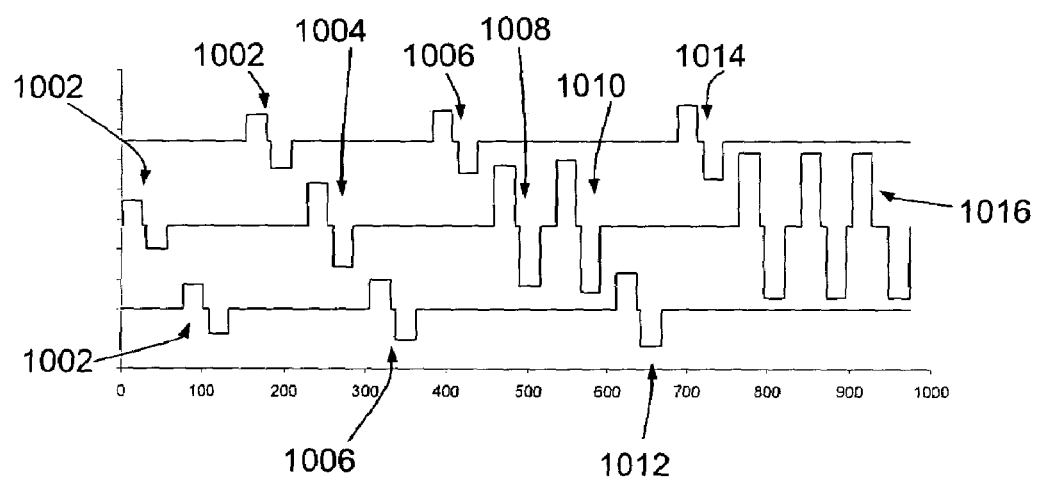
FIG. 10 shows non-repeating pulses of a pulse burst interleaved on two or more channels, in accordance with an embodiment of the present invention.
Figure 18A:
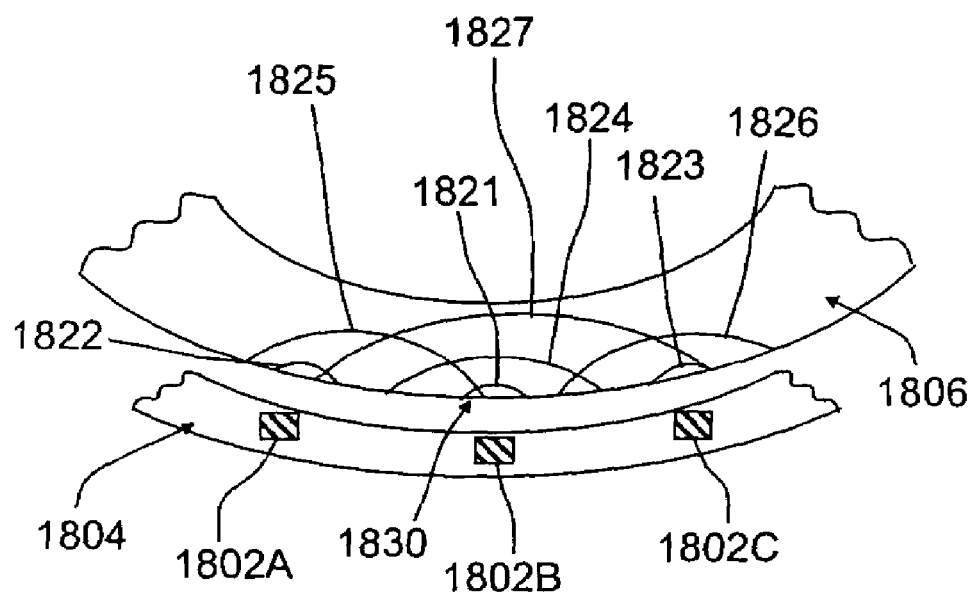
FIG. 18B shows a pulse burst used to generate the stimulation shown in FIG. 18A.
Figure 18B:
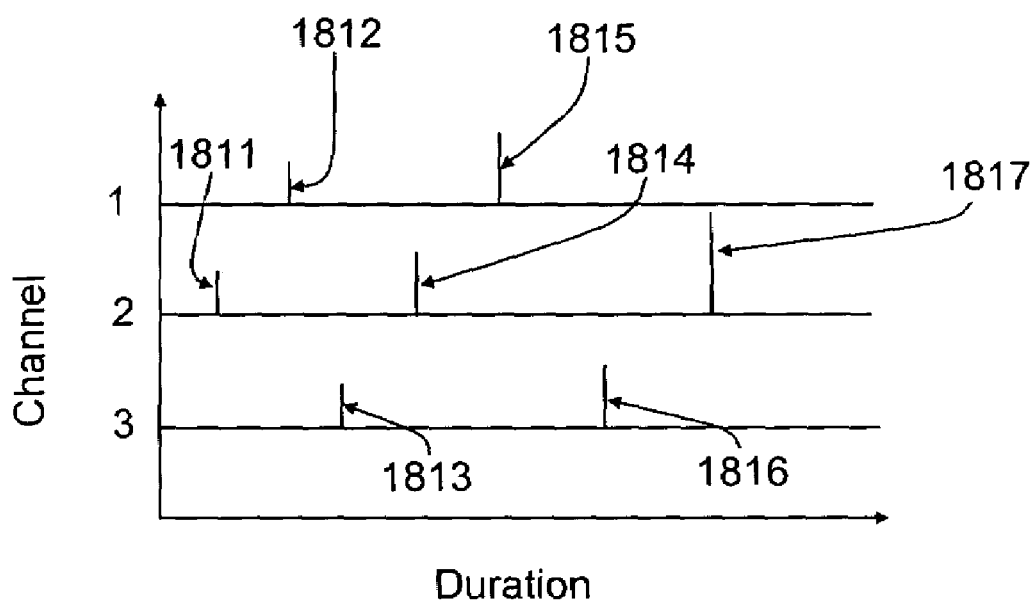

FIGS. 9 and 10 show individual pulses of a pulse burst that are interleaved over multiple channels to combine two or more channels into one channel. One advantage of such interleaving may be to increase the dispersed firing using multiple electrodes as shown in FIG. 18A and FIG. 18B. As shown in FIG. 9, pulse 904 begins on channel 1 and is repeatedly interleaved on channel 2 using substantially the same parameters, i.e. amplitude, duration, intra-pulse gap and waveform, etc. The next pulse 906 begins on channel 1 once pulse 904 is completed on channel 2. The process is repeated until the entire pulse burst is completed on both channels. Each pulse may have a width, IPG, waveform, amplitude, etc., as selected in accordance with the above-described parameters. The channels involved may stimulate adjacent nerve fibers that receive the stimulation signal from the electrodes.

FIG. 10 shows individual pulses of a pulse burst that are non-repeatedly interleaved on three channels. Pulse 1002 begins on channel 2 and is repeated using substantially the same parameters on channel 3, then channel 1. Next pulse 1004 begins on channel 2, but changes amplitude with pulse 1006 on channels 1 and 3. Also, multiple pulses, 1008 and 1010, may be used and not repeated on all of the channels with pulses 1012 and 1014. Multiple pulses 1016 may be repeated on one channel (channel 1 and 3 not shown). The number of pulses may vary depending on the desired firing rate and/or speech strategy. Also, the waveform of the pulse may vary between channels. Other parameters may be varied, such as the width, IPG, waveform, amplitude, etc. Embodiments of the present invention that use non-repeating individual pulses may be used in implementing arrays that contain approximately 22 or more stimulating channels. It should be appreciated by those skilled in the art that various combinations of non-repeating pulses might be used to define the pulse bursts of a stimulation signal.

FIG. 18A shows an example of the effect of interleaving a pulse burst, as shown in FIG. 18B, on multiple channels to increase dispersed firing. Three electrodes 1802 of an electrode array 1804 deliver stimulation signals to nerves within the spiral ganglion 1806. Electrode 1802A corresponds to channel 1 in FIG. 18B and so on. Electrode 1802B applies pulse 1811 to fiber population area 1821. A similar amplitude is repeated with pulses 1812 and 1813 on channels 1 and 3, and applied by electrodes 1802A and 1802C to fiber population areas 1822 and 1823, respectively. Next, the amplitude of pulse 1814 is increased from pulse 1811 and stimulates fiber population area 1824. Pulses 1815 and 1816 have a similar amplitude and stimulate fiber population areas 1825 and 1826, respectively. Some nerves may be stimulating by overlapping fiber population areas, such as shown with the overlap 1830 between fiber population areas 1821 and 1825. Finally, pulse 1817 with a relatively large amplitude is delivered by electrode 1802B to stimulate fiber population area 1827. Fiber population area 1827 overlaps most of the nerves that were stimulated by the previous pulses. The above embodiments of the present invention may create more dispersion by combing channels using an interleaving strategy rather than a single channel. Such embodiments may be combined with electrode arrays that have several electrodes for stimulating nerves or fibers.

Figure 11:
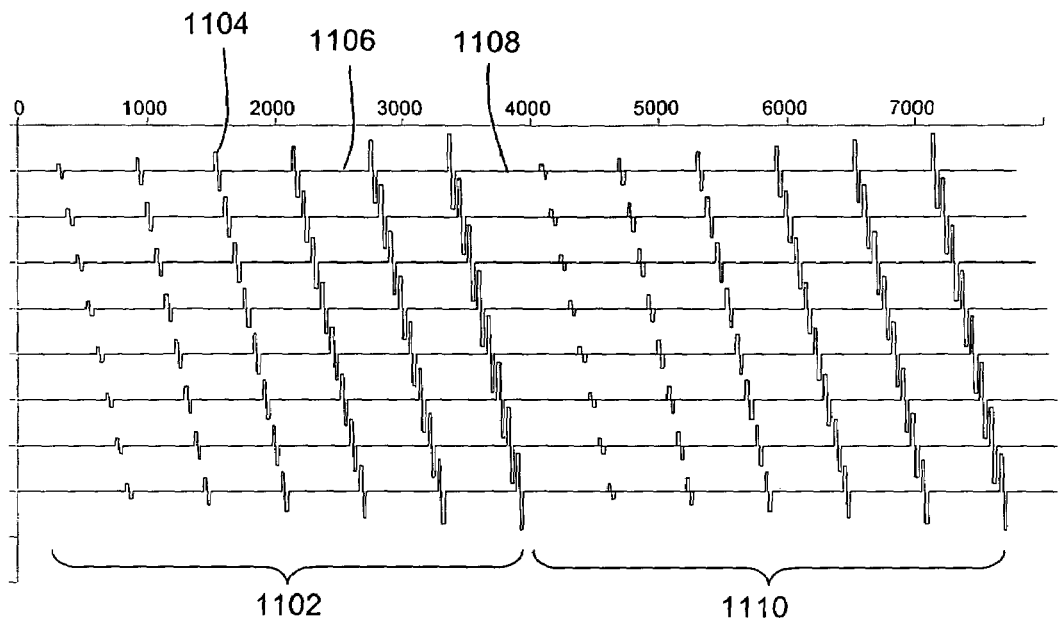
FIG. 11 shows individual pulses of a pulse burst interleaved on two or more channels, in accordance with an embodiment of the present invention.

FIG. 11 shows a strategy where ramping pulse burst 1102 having of pulses 1104 that are interleaved over multiple channels. Pulses 1104 are separated by an intra-pulse gap 1106. Each pulse 1104 may be repeated on each channel using substantially similar parameters. After an inter-pulse burst gap 1108, a second pulse burst 1110 may be interleaved on the channels. Intra-pulse gap 1106 and inter-pulse burst gap 1108 have different durations to define the period of ramping pulse burst 1102. Embodiments of the present invention that have interleaving pulses on multiple channels may be used, for example, with the CIS strategy to stimulate nerve fibers. Each pulse 1104 may have substantially the same parameters or different parameters from the other pulses in the pulse burst as discussed throughout this application. The intensity function of pulse burst 1102 or 1110 may use any of the intensity functions as discussed throughout this application. One advantage of having interleaving pulse bursts may be to decrease the overall rate over a sequential pulse burst thus making the stimuli more effective.

Figure 12:
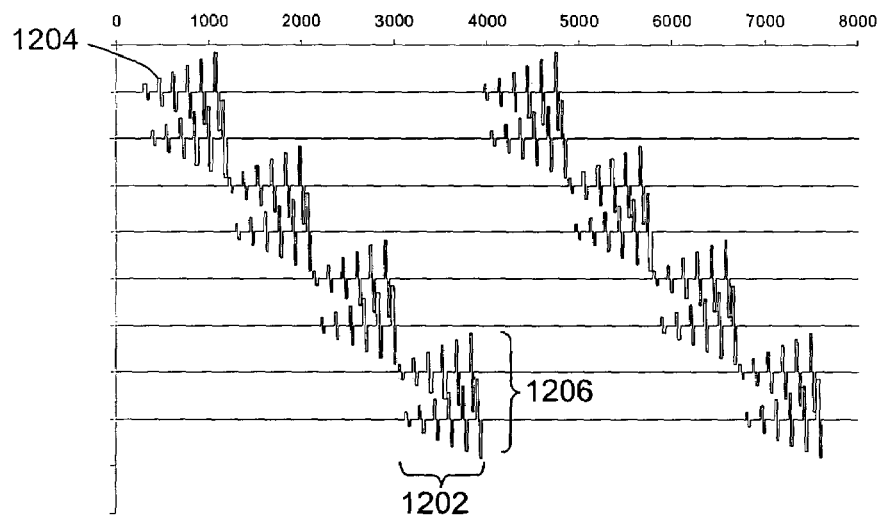
FIG. 12 shows two pulse bursts interleaved on two channels for producing a combined stimulation signal, in accordance with an embodiment of the present invention.

FIG. 12 shows a stimulation signal comprising a pulse burst 1202 having individual pulses 1204 interleaved on two channels. The interleaved stimulation may be combined in generating one stimulation signal 1206. This clearly shows the principle of combining two channels into one channel. The channels receiving the interleaved pulse burst may be adjacent or non-adjacent. SPEAK, ACE, CIS, Spread of Excitation strategy or similar strategies may employ a combined interleaved stimulation signal 1206.

Interleaving pulse bursts and pulses of a pulse burst as shown by FIGS. 8-12 on multiple channels may allow the present invention to decrease the overall pulse rate because pulses become more effective as they are occurring later with more chance to be outside the refractory period. It should be understood to those skilled in the art that more channels may be used when interleaving a pulse burst and thereby creating a new channel as shown in FIG. 18A. Depending on the number of current sources, multiple pulse bursts may be interleaved at substantially the same time on different channels. The above embodiments of the present invention may be used in conjunction with a low rate speech strategy that delivers less than approximately 500 pulses-per-second.

The varying parameters of pulse bursts and pulses of a pulse burst described in accordance with the present invention help to increase dispersed firing of the nerve fibers to mimic natural firing patterns. In addition, pulses bursts may enhance other physiological responses, such as enhancing temporal cues to a recipient.

It is known that hearing implants may be able to make use of both spectral (frequency or pitch) and temporal (time) cues when stimulating the nerve fibers. Temporal or time cues may provide information on prosody, intonation, stress, and segmental information, i.e. manner, place, gender, voicing cues, etc. Mimicking these temporal cues may be critical for differentiating sounds to the hearing implant recipient, especially with tonal languages (e.g. Mandarin and Cantonese) and music. Often two phonemes, such as the sound /a/ spoken by a male and female speaker or where change in the fundamental voice frequency of the same phonemic segment changes the lexical meaning in tonal languages, may have small difference in spectral cues, thus requiring the use of temporal cues to distinguish the sound. Conventional implants and speech strategies do not provide or enhance the necessary temporal cues needed to allow the implant recipient to distinguish temporal information. Thus, for example, recipients may only hear part of the music and fail to distinguish rhythm of music. Embodiments of the present invention allow the implant recipient to distinguish temporal cues by using different intervals or inter-pulse burst gaps between pulse bursts on low and high frequency channels.

In another embodiment, of the present invention enhanced temporal cues may be perceived by the recipient due to the generation of a simulation signal having pulse bursts that have relatively longer inter-pulse burst gaps on low frequency channels and relatively shorter inter-pulse burst gaps on high frequency channels.

Figure 13:
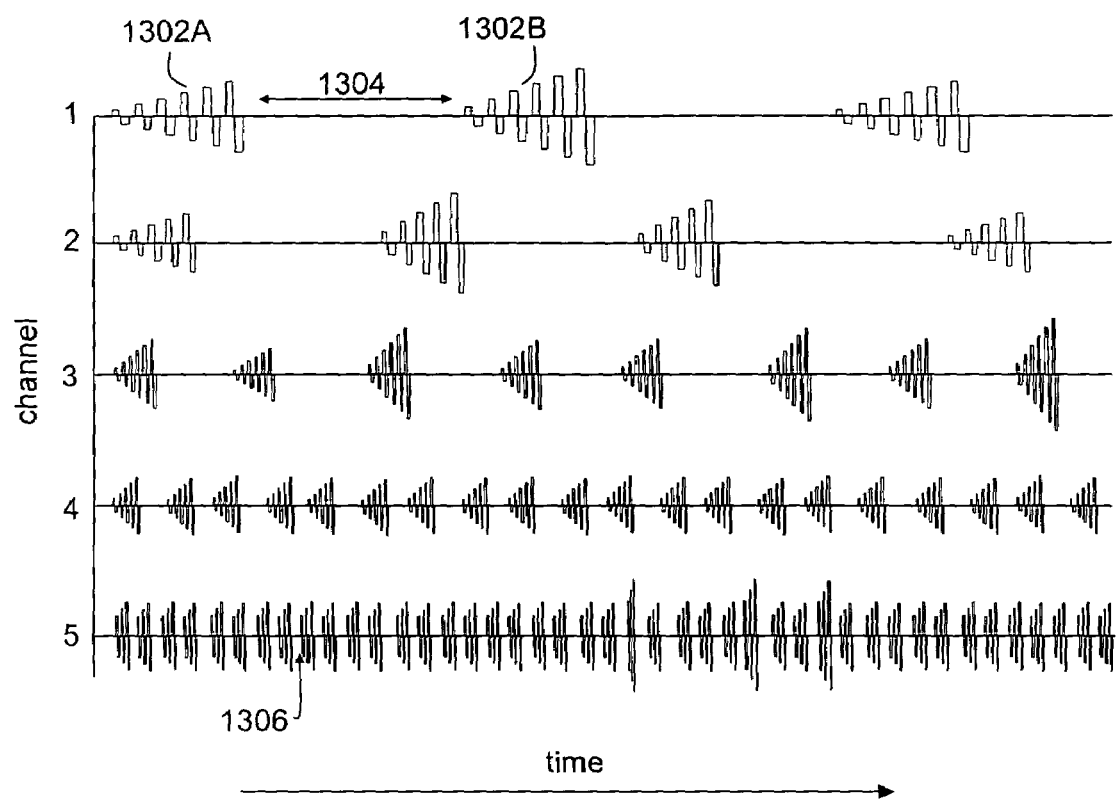
FIG. 13 shows several pulse bursts having varying intervals depending on the frequency of the channel, in accordance with an embodiment of the present invention.

FIG. 13 shows five channels that are stimulated with varying pulse bursts depending on the channel's frequency.

The use of different pulse bursts and inter-pulse burst gaps may provide the recipient additional temporal cues on the low frequency channels, i.e. below 500 Hz. Low frequency channels may use pulse bursts that have relatively greater duration and longer inter-pulse burst gaps than high frequency channels. For example, on channel 1, a low frequency channel, pulse burst 1302A is separated by an inter-pulse burst gaps 1304 from pulse burst 1302B that is larger than inter-pulse burst gaps 1306 used in channel 5, a high frequency channel. In addition, pulse bursts 1302 used on each channel may have varying parameters and intensity functions in accordance with embodiments of the present invention. Inter-pulse burst gaps 1304 between pulse bursts 1302 may be adapted to the center frequency to the Fast Fourier Transform (FFT), which may be processed in accordance with the strategy. This might improve temporal information for the recipient. Additional channels may be used depending on the capabilities of the electrode array and hearing implant. Also, the channels selected for applying the pulse burst may be non-adjacent or non-consecutive, depending on the strategy. Pulse bursts 1302 may be interleaved on channels, or delivered simultaneously on one or more the channels. In the embodiment illustrated in FIG. 13, the width of the pulses in the pulse bursts transmitted on one channel is different than the width of the pulses in the pulse bursts transmitted on other channels. As one of ordinary skill in the art would appreciate, however, is that in alternative embodiments the pulse bursts transmitted on all channels have pulses of the same width.

The lower frequency channels, for example, those between 200 Hz and 500 Hz, may use pulse bursts with greater durations that those channels that are above 500 Hz. These low frequency channels may provide the implant recipient with additional temporal information which enhances the overall perceived sound. In addition, as illustrated by FIG. 13, each pulse burst on each channel is discretely defined by the difference of inter-pulse burst gaps v. intra-pulse gaps.

Each parameter for a pulse bursts described above may be further tested using coding strategies, i.e. SPEAK or ACE, and the Nucleus Implant Communicator (NIC) software toolbox to achieve optical perception performance. One advantage of certain embodiments of the present invention may be to increase the speech (particularly speech in noise and speech in tonal languages) and music perception of recipients.

As one of ordinary skill in the art would appreciate, the pulses of a pulse burst may be referred to as a "pulse train" and the stimulation signal may be referred to as comprising a series of such pulse trains.

Although the present invention has been fully described in conjunction with the certain embodiment thereof with reference to the accompanying drawings, it is to be understood that various changes and modifications may be apparent to those skilled in the art. Such changes and modifications are to be understood as included within the scope of the present invention.

What is claimed is:

1. A method of stimulating auditory nerve fibers comprising:
generating a stimulation signal comprising a plurality of pulse bursts, each said pulse burst comprising a succession of pulses, wherein at least one of said successive pulses and its immediate preceding pulse have at least one parameter that is different;
distributing a selected pulse burst from said plurality of pulse bursts to a selected electrode of one or more electrodes operatively coupled to a selected group of auditory nerve fibers wherein the at least one different parameter causes said succession of pulses to deliver a charge to the auditory nerve fibers that causes firings in the auditory nerve fibers that are substantially stochastic in time and dispersed along the auditory nerve fibers, wherein the firings occur at substantially normal physiological rates and wherein said plurality of pulse bursts are separated in one or more of space and time to provide substantially normal recovery periods.

2. The method of claim 1, wherein said generating said stimulation signal comprises:
generating said stimulation signal in accordance with an implemented speech processing strategy.

3. The method of claim 2, wherein said implemented speech processing strategy comprises an implemented low-rate speech processing strategy.

4. The method of claim 3, wherein said stimulation signal has a pulse rate of less than approximately 500 pulses per second.

5. The method of claim 1, wherein one or more of the plurality of pulse bursts is a ramped pulse burst.

6. The method of claim 5, wherein said ramped pulse burst has an approximate linear intensity function.

7. The method of claim 6, wherein said approximate linear intensity function of said ramped pulse burst is a linearly increasing intensity function.

8. The method of claim 7, wherein said linearly increasing intensity function of said ramped pulse burst is progressively increasing across successively occurring ramped pulse bursts.

9. The method of claim 5, wherein said ramped pulse burst has an approximate exponential intensity function.

10. The method of claim 5, wherein said ramped pulse burst has a staggered intensity function.

11. The method of claim 1, wherein one or more successive pulses of said succession of pulses comprise a biphasic pulse.

12. The method of claim 1, wherein one or more successive pulses of said succession of pulses comprise a monophasic pulse.

13. The method of claim 1, wherein one or more successive pulses of said succession of pulses have a substantially square waveform.

14. The method of claim 1, wherein one or more successive pulses of said succession of pulses have a substantially sinusoidal waveform.

15. The method of claim 1, wherein one or more successive pulses of said succession of pulses have a substantially sawtooth waveform.

16. The method of claim 1, wherein said at least one different parameter comprises a duration.

17. The method of claim 1, wherein said least one different parameter comprises an amplitude.

18. The method of claim 1, further comprising:
distributing said plurality of pulse bursts across said one or more electrodes such that said succession of pulses of at least one of said plurality of pulse bursts occurring on said selected electrode are interleaved with said succession of pulses of at least one other of said plurality of pulse bursts occurring on a different electrode of said one or more electrodes.

19. The method of claim 18, wherein distributing said plurality of pulse bursts across said one or more electrodes comprises:
distributing said plurality of pulse bursts across said selected and different electrode such that said succession of pulses of said at least one of said plurality of pulse bursts are repeatedly interleaved with said succession of pulses of said at least one other of said plurality of pulse bursts.

20. The method of claim 1, wherein said plurality of pulses bursts is sequentially distributed on said one or more electrodes.

21. The method of claim 1, wherein at least two successive pulses of the succession of pulses are simultaneously distributed on two or more of said one or more electrodes.

22. The method of claim 1, wherein distributing said plurality of pulse bursts to enhance-temporal cues when stimulating said auditory nerve fibers.

23. The method of claim 22, wherein said one or more electrodes comprises one or more high frequency electrodes and one or more low frequency electrodes each operatively coupled to said auditory nerve fibers which responds to high frequency stimulation signals or low frequency stimulation signals, respectively, and
wherein a first portion of said plurality of pulse bursts are distributed on said one or more low frequency electrodes and a second portion of said plurality of pulse bursts are distributed on said one or more high frequency electrodes.

24. The method of claim 23, wherein said one or more low frequency electrodes are operatively coupled to said auditory nerve fibers that respond to stimulation below 500 Hz.

25. The method of claim 23, wherein said one or more high frequency electrodes are operatively coupled to said auditory nerve fibers that respond to stimulation above 500 Hz.

26. The method of claim 23, wherein said first portion of said plurality of pulse bursts have a longer duration than said second portion of said plurality of pulses bursts.

27. The method of claim 23, wherein said first portion of said plurality of pulse bursts have a longer interval than said second portion of said plurality of pulses bursts.

28. The method of claim 23, wherein said succession of pulses of said first portion of said plurality of pulse bursts have a longer duration than said succession of pulses of said second portion of said plurality of pulses bursts.

29. A method of stimulating nerve fibers using electrodes operatively coupled to the nerve fibers comprising:
generating a stimulation signal comprising a first plurality of pulse bursts having a first duration and a second plurality of pulse bursts having a second duration that is less than said first duration, wherein the first plurality of pulse bursts comprises a first succession of pulses having at least one different first parameter for each successive pulse, and wherein the second plurality of pulse bursts comprises a second succession of pulses having at least one different second parameter for each successive pulse;
distributing said first plurality of pulse bursts across one or more of said electrodes operatively coupled to first nerve fibers responsive to low frequency stimulation such that the at least one different first parameter of each said successive pulse causes said first succession of pulses to deliver a first charge to said first nerve fibers, wherein said first charge causes stochastic and dispersed firing in said first nerve fibers; and
distributing said second plurality of pulse bursts across one or more of said electrodes operatively coupled to second nerve fibers responsive to high frequency stimulation such that the at least one different second parameter of each said successive pulse causes said second succession of pulses to deliver a second charge to said second nerve fibers, wherein said second charge causes stochastic and dispersed firing in said second nerve fibers.

30. The method of claim 29, wherein the first and second nerve fibers are auditory nerve fibers.

31. The method of claim 29, wherein said first nerve fibers responsive to low frequency stimulation are responsive to stimulation below 500 Hz.

32. The method of claim 29, wherein said second nerve fibers responsive to high frequency stimulation are responsive to stimulation above 500 Hz.

33. The method of claim 29, wherein a speech processor implementing a low-rate speech processing strategy generates said stimulation signal.

34. The method of claim 29, wherein one or more of said first plurality of pulse bursts is ramped.

35. A prosthetic hearing device, comprising:
means for generating a stimulation signal from an ambient sound;
means for defining one or more pulse bursts in said stimulation signal, each of the one or more pulse bursts comprising a succession of pulses, wherein at least one of said successive pulses and its immediate preceding pulse have at least one parameter that is different;
means for distributing a selected pulse burst from said pulse bursts to a selected electrode from one or more electrodes operatively coupled to a selected group of auditory nerve fibers, wherein the at least one different parameter causes said succession of pulses to deliver a charge to the auditory nerve fibers that causes firings in the nerve fibers that are substantially stochastic in time and dispersed along the auditory nerve fibers, wherein the firings occur at substantially normal physiological rates and wherein said plurality of pulse bursts are separated in one or more of space and time to provide substantially normal recovery periods.

36. The prosthetic hearing device of claim 35, wherein the one or more pulse bursts each is a ramped pulse burst.

37. The prosthetic hearing device of claim 35, wherein the nerve fibers are auditory nerve fibers.

38. The prosthetic hearing device of claim 35, wherein said means for distributing said pulse bursts across one or more electrodes comprises:
means for distributing a first plurality of said one or more pulse bursts across one or more electrodes operatively coupled to nerve fibers responsive to low frequency stimulation; and
means for distributing a second plurality of said one or more pulse bursts across one or more electrodes operatively coupled to nerve fibers responsive to high frequency stimulation.

39. The prosthetic hearing device of claim 38, wherein said nerve fibers responsive to low frequency stimulation are responsive to stimulation below 500 Hz, and said nerve fibers responsive to high frequency stimulation are responsive to stimulation above 500 Hz.

* * * * *